United States Patent
Maiwald et al.

(10) Patent No.: US 9,950,554 B2
(45) Date of Patent: Apr. 24, 2018

(54) APPLICATION PEN AND METHOD FOR THE PRODUCTION THEREOF

(71) Applicant: SIKA TECHNOLOGY AG, Baar (CH)

(72) Inventors: Dana Maiwald, Zurich (CH); Dominique Burkard, Gretzenbach (CH)

(73) Assignee: SIKA TECHNOLOGY AG, Baar (CH)

(*) Notice: Subject to any disclaimer, the term of this patent is extended or adjusted under 35 U.S.C. 154(b) by 0 days.

(21) Appl. No.: 14/346,402

(22) PCT Filed: Sep. 19, 2012

(86) PCT No.: PCT/EP2012/068449
§ 371 (c)(1),
(2) Date: Mar. 21, 2014

(87) PCT Pub. No.: WO2013/041573
PCT Pub. Date: Mar. 28, 2013

(65) Prior Publication Data
US 2014/0301765 A1  Oct. 9, 2014

(30) Foreign Application Priority Data

Sep. 23, 2011 (EP) .................................... 11182576

(51) Int. Cl.
*B43K 5/00* (2006.01)
*A61F 13/40* (2006.01)
(Continued)

(52) U.S. Cl.
CPC ................ *B43K 5/00* (2013.01); *A45D 34/04* (2013.01); *A61M 35/006* (2013.01); *B05C 17/00* (2013.01);
(Continued)

(58) Field of Classification Search
CPC ... B05C 85/42; A61M 35/003; A61M 35/006; B43M 11/06; A45D 34/04; B65D 47/42
(Continued)

(56) References Cited

U.S. PATENT DOCUMENTS 1,297,675 A * 3/1919 Garvey .................. B65D 47/42
401/196
2,832,087 A    4/1958 McEwan
(Continued)

FOREIGN PATENT DOCUMENTS

FR           2769506 A1    4/1999
WO    WO-2010/003518 A1    1/2010

OTHER PUBLICATIONS

International Search Report (German and English) for PCT/EP2012/068449, ISA/EP, Rijswijk, NL, dated Oct. 19, 2012 (6 pages).
(Continued)

*Primary Examiner* — Jennifer C Chiang
*Assistant Examiner* — Bradley Oliver
(74) *Attorney, Agent, or Firm* — Buchanan Ingersoll & Rooney PC

(57) ABSTRACT

An application pen includes a hollow pen body made of plastic having a closed end and an open end and an applicator head on the open end of the pen body. The applicator head has a foam, felt or fiber body. The applicator head has an end section that fits into the open end of the pen body. The pen body has mechanical fastening means for positive-locking and/or friction-locking engagement with the outer circumference of the end section of the applicator head without deformation of the end section of the applicator head protruding into the open end of the pen body.

19 Claims, 3 Drawing Sheets

(51) Int. Cl.
   *B43M 11/06* (2006.01)
   *B65D 47/42* (2006.01)
   *B05C 17/00* (2006.01)
   *A45D 34/04* (2006.01)

(52) U.S. Cl.
   CPC ............. *B43M 11/06* (2013.01); *B65D 47/42* (2013.01); *A45D 2200/1009* (2013.01); *Y10T 29/49826* (2015.01)

(58) Field of Classification Search
   USPC .................................................. 401/132, 133
   See application file for complete search history.

(56) References Cited

U.S. PATENT DOCUMENTS

| | | | |
|---|---|---|---|
| 2,967,319 A | | 1/1961 | Bumpus et al. |
| 3,152,352 A | | 10/1964 | Kosik, Jr. |
| 4,957,385 A | | 9/1990 | Weinstein |
| 5,775,826 A | * | 7/1998 | Miller .................... A45D 34/04 401/132 |
| 2005/0054967 A1 | | 3/2005 | Ashe et al. |
| 2005/0111900 A1 | | 5/2005 | Fazzolari et al. |
| 2005/0191113 A1 | | 9/2005 | Frazier |
| 2011/0159457 A1 | | 6/2011 | Offermann |

OTHER PUBLICATIONS

Written Opinion of the ISA (German) for PCT/EP2012/068449, ISA/EP, Rijswijk, NL, dated Oct. 19, 2012 (7 pages).

Second Office Action dated Jul. 1, 2016 issued by the State Intellectual Property Office of the People's Republic of China in corresponding Chinese Patent Application No. 201280045979.3, and English language translation of Office Action (12 pages).

Notification of the Third Office Action dated Nov. 28, 2016 issued by the State Intellectual Property Office of the People's Republic of China in corresponding Chinese Patent Application No. 201280045979.3 (15 pages including partial English translation).

Office Action dated Feb. 15, 2018, by the European Patent Office in corresponding European Patent Application No. 12759476.0 and an English Translation of the Office Action. (9 pages).

\* cited by examiner

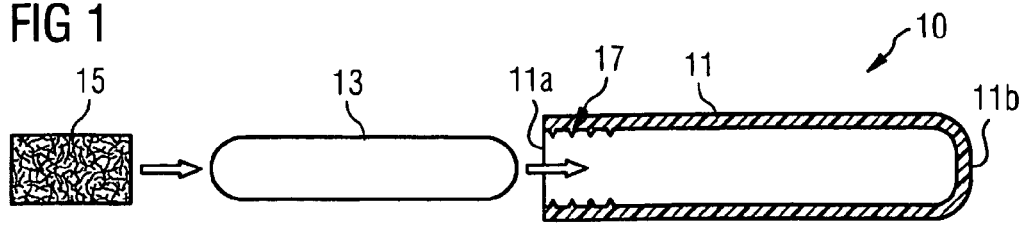
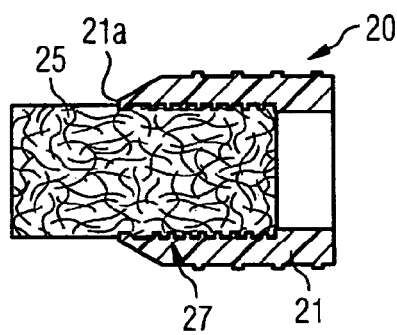
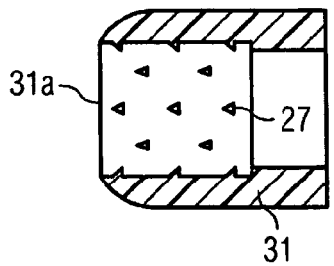
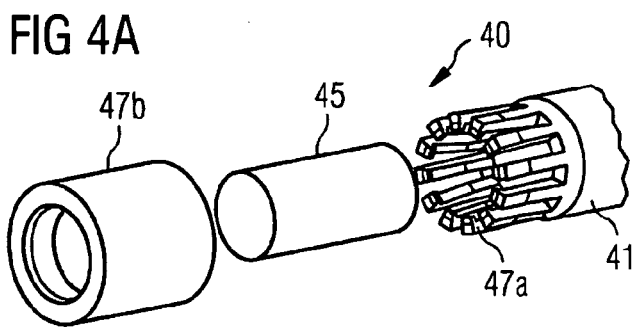
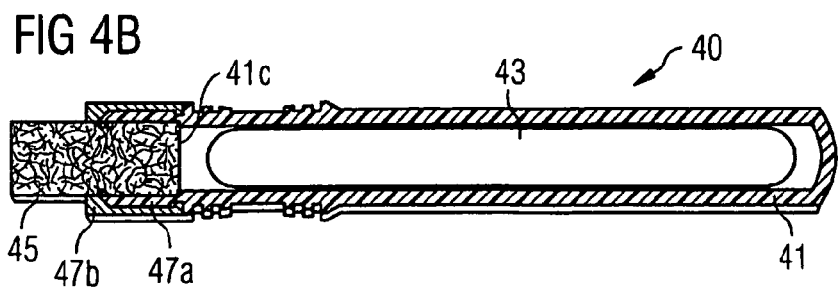

APPLICATION PEN AND METHOD FOR THE PRODUCTION THEREOF

CROSS-REFERENCE TO RELATED APPLICATIONS

This application is a 371 U.S. National Stage of International Application No. PCT/EP2012/068449, filed Sep. 19, 2012, which claims priority to European Patent Application No. 11182576.6, filed Sep. 23, 2011. The disclosures of the above applications are incorporated herein by reference.

TECHNICAL FIELD

The invention relates to an application pen for dispensing a liquid, in particular in a punctiform or planar manner, comprising a hollow pen body made of plastic having a closed end and an open end and an applicator head sitting on the open end of the pen body, which applicator head is made, in particular, from a foam, felt, fiber body, or a porous plastic. It relates moreover to a method for producing such an application pen.

PRIOR ART

Preliminary treatment means for producing adhesive connections and corrosion protection are usually offered in packages which consist of an aluminum bottle, a polyethylene (PE) bowl and a screw connection of the bottle, which is made of polypropylene (PP). In the field of one-time applications, aluminum tubes or primer pens and activator pads each having a very small content are also offered.

Application pens of the above-described type have been available commercially for quite some time and are in practical use. The applicator head in the case of such pens is usually welded to the pen body, which requires a thermal process step in the manufacture, which entails certain disadvantages with regard to the process management. From US 2005/0191113 A1, a construction design of the application pen is known, wherein the open end comprises a constriction produced by heating, by means of which the applicator head (constricted in the same manner) is held on the pen body and at the same time a certain control function is fulfilled with regard to the dispensing of liquid from the application pen.

The invention is therefore based on the problem of providing an improved application pen of the type according to the classification, which is produced particularly cost effectively and which can be used easily, flexibly and reliably.

DISCLOSURE OF THE INVENTION

This problem is solved by an application pen having the features of Claim 1. Moreover, a method is provided having the features of Claim 13. Advantageous variants of the idea of the invention are the subject matter of the dependent claims.

The invention includes the thought of departing from a constriction which considerably deforms the applicator head and which limits the flow of liquid flow from the pen body at the open end of the pen body for fastening the applicator head. Furthermore, it instead includes the idea of applying the required holding force onto the outer wall of the applicator head without substantial deformation thereof, namely in particular over the larger portion of the end section protruding into the open end of the pen body. Accordingly, fastening means are provided on the pen body, which are in superficial positive and/or friction lock with the outer surface of the applicator head.

In an advantageous design of the invention, the applicator head or in any case its end section has, in the inserted state, a prismatic or cylindrical basic shape. The shape can be in particular that of a three-, four- or six-sided prism having rounded edges, and said prism can be beveled at the free end of the applicator head or (for a more linear dispensing of liquid) pointed. It is understood that parts or sections of the pen body can penetrate, as fastening means for establishing the mentioned positive lock, into this basic shape, but this penetration should not substantially change the basic shape.

In a more particular design, it is provided that at least the end section of the applicator head and at least the open end of the pen body are shaped cylindrically, and the fastening means have an inner thread on the pen body, which cuts into the circumference of the end section of the applicator head. In particular, the thread pitches can be substantially triangular or trapezoidal in cross section. In this design, the applicator head is not slid axially into the pen body, instead it is inserted with a rotating motion into said applicator head, which brings about a cutting or pushing of the thread into the surface of the applicator head. In particular, a stop margin here delimits the penetration depth of the applicator head on the inner wall of the pen body.

In another design, islet-like projections are formed on the inner wall of the pen body close to the open end, which engage in the circumference of the end section of the applicator head and act in particular as barbed hooks, in such a way that they can easily be overridden by the applicator head during the insertion, but offer strong resistance against the pulling out of the applicator head. Depending on the concrete design of the shape of the projections, the insertion of the applicator head into the open pen body end can occur axially or again with a turning motion.

In an additional design of the invention, the fastening means comprise claws formed on the open end of the pen body, which, in the starting state, are spread open for the introduction of the end section of the applicator head. Moreover, they comprise a closing sleeve which can be shifted over the claws in their spread open state and which is shaped so that, as it is shifted, it pushes the claws, in a punctiform manner, into the outer wall of the end section of the applicator head, without substantially reducing the cross section of the applicator head and thus the cross section of flow of the liquid contained in the pen. In a first embodiment, the closing sleeve is formed over predetermined rupture points on the pen body. In a second embodiment, the closing sleeve is designed as a separate part and in particular packaged together with the application pen.

In a design similar to the above-mentioned design, instead of claws, branches having inward-directed islet-like projections are spread open in the initial state and pressed by means of a closing sleeve against the outer circumference of the end section of the applicator head. The islet-like projections penetrating into the material of the applicator head act in a manner similar to that of the above-mentioned claws.

In a design that is particularly important in practice, the pen body is designed for receiving a hard ampule, and its wall is sufficiently flexible in order to break the ampule held in the pen body and as a result bring about the discharge of the liquid from the ampule into the interior of the pen body. Such application pens have great market relevance particularly for dispensing primers or similar preliminary treatment agents for corrosion protection or adhesion, for example, in the field of the production of car glazing.

In an advantageous embodiment of this design, the outer surface of the wall of the pen body is structured with at least one, in particular annular, recess and/or elevation. More specifically, the outer surface of the wall of the pen body comprises a plurality of annular recesses, which mark a constriction area of the pen body. In this constriction area, the wall of the pen body is advantageously pushed in and/or bent with the fingers, or it may also be bent over an edge of a hard body (for example, the edge of the table), in order to rupture the ampule held therein. Alternatively or in combination with the above-mentioned embodiment, symbols can be formed into the outer surface of the wall of the pen body, guiding the user to exert local pressure on the pen body in order to break the ampule.

In an additional embodiment, close to the open end of the pen body, a plurality of annular recesses or similar structural elements are provided, which define a gripping area of the application pen. The instruction elements incorporated in the material of the pen body can make any additional gluing or printing of corresponding marks or instructions unnecessary and thus lower the manufacturing costs.

The method according to the invention is characterized by a purely mechanical fastening of the applicator head to the open pen end, without any thermal sealing or deforming step. In a first embodiment of the method, the mechanical fastening means at the open pen end are already operative in the initial state, and the applicator head is thus pushed or rotated inward against the (predetermined limited) resistance of the fastening means into the pen body. In an alternative embodiment, the fastening means have a certain movability, and, at the time of the insertion of the applicator head, they are substantially in an inoperative initial state. It is only after the loose insertion of the applicator head into the open pen end that they are moved—again in a purely mechanical manner—in such a way that they engage in the circumference of the end section of the applicator head and bring about the desired positive and/or friction lock there.

DESCRIPTION OF THE DRAWINGS

Advantages and uses of the invention will become apparent in the following description of preferred embodiment examples in reference to the figures:

FIG. 1 shows a schematic diagram for the purpose of explaining the invention, in the form of a longitudinal section of an application pen, FIG. 2 shows a detailed view (longitudinal section) of the open end of an application pen according to the invention, FIG. 3 shows a detailed view (longitudinal section) of an additional embodiment of the application pen according to the invention, FIGS. 4A and 4B show a perspective partial view as well as a longitudinal section for the purpose of explaining an additional embodiment of the invention.

FIG. 1 shows a sketch-like longitudinal section of an application pen 10 for dispensing a primer as corrosion protection for the preparation of vehicle window adhesions, application pen which contains a substantially stiff pen body 11 made of thermoplastic material but having some deformability, a glass ampule 13 containing the primer, for insertion into the pen body 11, and an applicator head 15, for the punctiform or planar application of the primer, which consists of a porous material, in particular a porous plastic, foam, a felt or fiber body. The represented parts can have a substantially cylindrical or also prismatic basic shape. The pen body 11 has an open end 11a and a closed end 11b, and, on its inner wall, close to the open end, fastening means 17 for the applicator head 15 are provided, which bring about a positive or friction lock. Embodiments of the fastening means are described further below. In a variant which is not shown here the pen body has, at the closed end in the back, a small projection which delimits the depth of insertion of the ampule.

FIG. 2 shows, as an embodiment, only the open end 21a of the pen body 21 of an application pen 20 with inserted applicator head 25. Here, an inner thread 27 is incorporated into the inner wall of the end area of the pen body 21, as a fastening means for the applicator head 25, and the applicator head 25 is connected by rotating inward from the open end to the pen body, wherein the thread 27 cuts into its outer wall. At the end of the pen 27, the inner diameter of the pen body 21 is slightly reduced, as a result of which (in a manner similar to the one described in reference to FIG. 4B), a stop for the applicator head 25 is formed.

FIG. 3 shows, in a modified design, a pen body 31, close to the open end of which, as a fastening means, in order to achieve a sufficiently firm insertion of an applicator head (not shown here), islet-like projections 27 are provided which, in a cross section as well as in a top view, have an approximately triangular shape, and which engage like barbed hooks into an inserted applicator head.

FIGS. 4A and 4B show an application pen 40, as an additional design of the invention, in an exploded perspective view (partial view) and in a longitudinal section. An approximately cylindrical pen body 41 contains an ampule 43, and, on its front end, a felt applicator 45 is fastened by means of a ring of claws 47a and a closing sleeve 47b. In FIG. 4A, an initial state of the pen body 41 is shown, as it is produced during the forming process, and in which the claws 47a are spread apart slightly toward the outside. This allows a practically resistance-free sliding of the applicator head 45 into the open end of the pen body. After the sliding in, during which the insertion depth is limited by an annular flange 41c used as a stop or by the ampule in the pen body, the separately produced closing sleeve 47b is also slid from the open end over the claw ring 47a and it pushes the claws inward into the material of the applicator head 45. The closing sleeve 47b itself maintains a friction lock with the outer surfaces of the claws and thereby stays on the pen end, or else a thread pitch or bayonet closure or the like is provided.

FIGS. 5A and 5B show, as a design that is modified compared to the design according to FIGS. 4A and 4B, an additional application pen 50 in a perspective representation in the initial state and in the usage state. Instead of a claw ring, here two half rings 57a acting as claws, which are spread open in the initial state, are formed on the open end of the pen body 51. On its closed end, a closing sleeve 57b is formed over plastic connectors (not labeled separately), which are easy to break and which release the closing sleeve 57*b* after they are broken. After the applicator head 55 has been introduced into the open end of the pen body, from its closed end, the closing sleeve 57*b*, which has been detached from the pen body, is slid forward in the direction of the open end; in the process it engages with the half rings 57*a* and pushes them against the circumference of the applicator head 55 and with the slightly inward protruding front edges slightly into the material of said applicator head. As a result, in the usage state shown in FIG. 5B, the applicator head is held by positive locking on the pen body 51.

FIG. 6A shows an additional application pen 60, whose basic shape, as in the above-described application pens, is cylindrical (just like the basic shape of the applicator head 65). A circumferential indentation 61*d* in the outer wall signals to the user, in a sense of a guide for the user, to use manual pressure there or possibly to apply a tool thereto, in order to rupture the ampule (not shown) contained in the pen body and as a result bring about the discharge of the liquid contained therein into the interior of the pen body. In addition, the pen body, in its front half at the end of which the applicator head 65 is arranged, is provided with a large-surface concavity 61*e*. Here, the user should grip the pen, and the concavity facilitates the gripping and the guiding of the pen over an area to be coated with the liquid.

FIG. 6B shows, as a modified design, in a detailed view, the middle area of an additional application pen 60', in which, on both sides of the above-mentioned indentation 61*d*, arrow symbols 61*f* are formed into the outer wall of the pen body 61'. Their purpose is to signal to the user additionally that he should apply manual pressure here and in which direction. The above-mentioned concavity area in the front part of the pen body is here provided additionally with annular recesses 61*g* and, to distinguish it from the unstructured concavity area 61*e* of the application pen 60 in FIG. 6A, it is marked with the reference numeral 61*e'*. The additional annular recesses 61*g* facilitate holding of the application pen, when the user is wearing gloves, for example, or if the pen is wet.

FIG. 7 shows an additional application pen 70, whose design is similar to that shown in FIG. 6A and described above, but whose gripping area is structured by ellipsoid elevations 71*g* which—in contrast to the annular recesses 61*g* of the design according to FIG. 6B—do not extend over the circumference of the pen, but extend merely to the side along the wall. In addition, an applicator head 75 is used here, whose basic shape is in fact cylindrical, but which has a bevel 75*a* at its free end.

FIG. 8 shows an additional application pen 80, in which the cylindrical outer shape of the pen body 81 is maintained over its entire length (with the exception of the immediate vicinity of the open end). Here, in the front region, raised rings 81*g* are formed to facilitate the gripping and guiding of the pen, and in the middle area, annular marks 81*f* are provided (on both sides), the purpose of which is to indicate to the user an appropriate pressure point for rupturing the ampules received in the pen body.

FIG. 9 represents various sketch-like designs of applicator heads, which can be used in an application pen according to the invention. The representations are self explanatory, so that a verbal description can be dispensed with here. It should be understood that the shaping, at least in the area of the open end of an associated pen body, has to be adapted to the outer shape of the end of the respective applicator head. However, for the rest of the pen body, the outer shape can differ, and the basic shape of the end section of the applicator head can also be different from the shape in the area of its free end, by means of which the liquid is dispensed onto a surface.

Figure 5A:
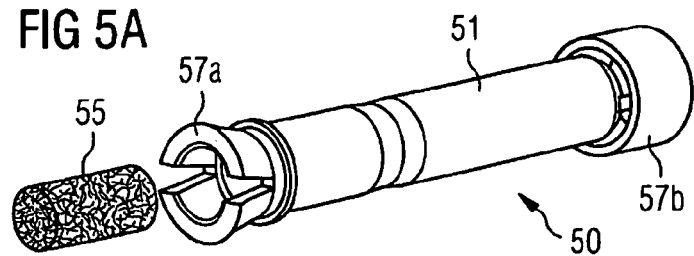
FIGS. 5A and 5B show two perspective representations for the purpose of explaining an additional embodiment of the invention.
Figure 5B:
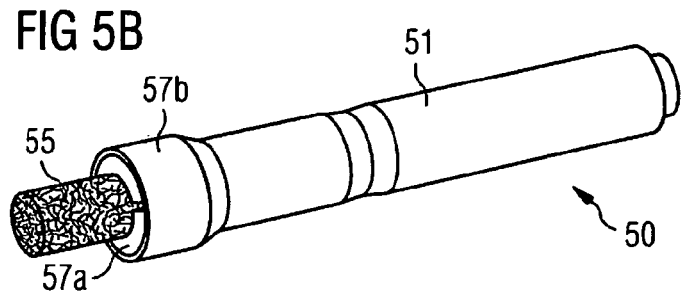
Figure 6A:
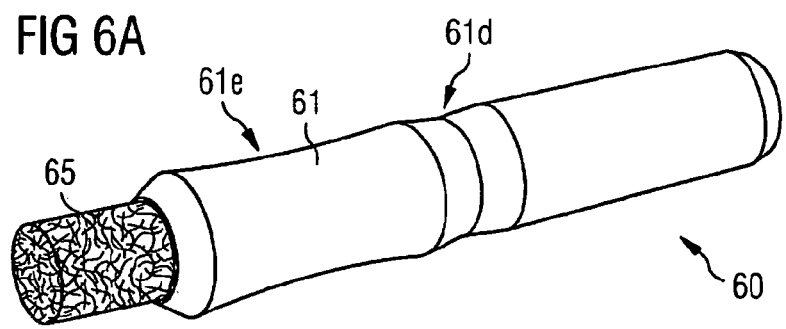
FIGS. 6A and 6B show a perspective overall view and a detailed view, respectively, of two additional embodiments of the application pen according to the invention.
Figure 6B:
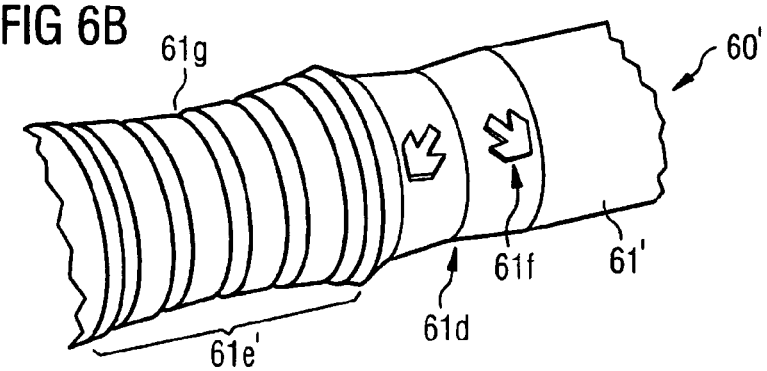
Figure 7:
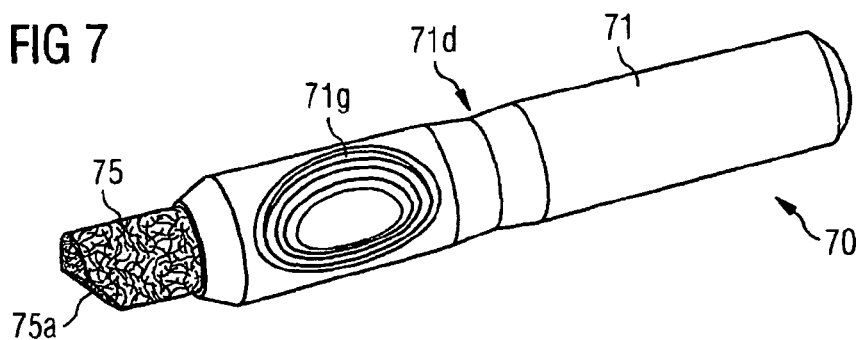
FIG. 7 shows a perspective overall view and a detailed view, respectively, of an additional embodiment of the application pen according to the invention.
Figure 8:
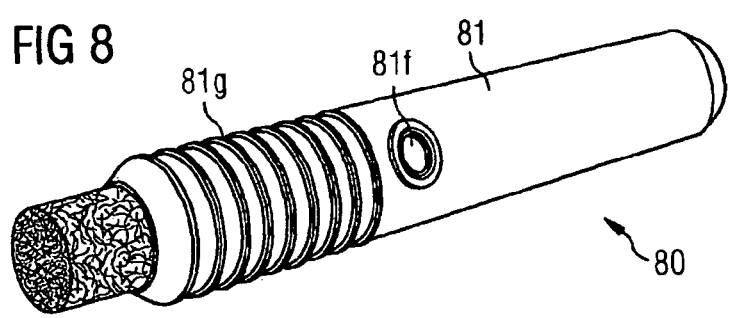
FIG. 8 shows a perspective overall view and a detailed view, respectively, of an additional embodiment of the application pen according to the invention.
Figure 9:
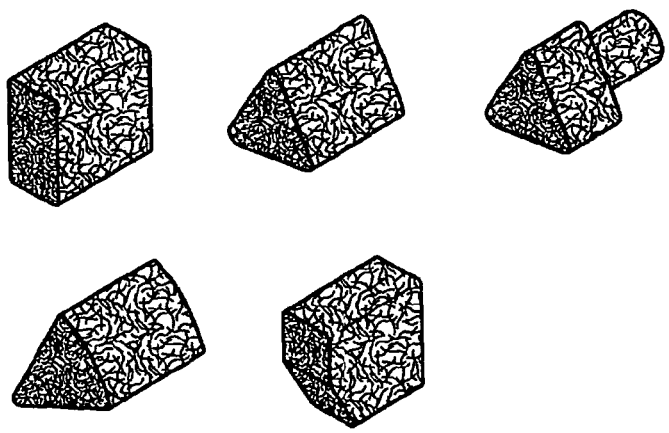
FIG. 9 shows a sketch-like representation of differently shaped applicator heads by means of which the invention can be implemented.

The design of the invention is not limited to these examples; instead, it may also be applied in a plurality of variants that fall within the scope of a person skilled in the art.

The invention claimed is:

1. An application pen for dispensing a liquid comprising:
    a hollow pen body configured for receiving an ampule containing liquid, the pen body being made of plastic and having a closed end and an open end, a longitudinal direction of the application pen extending from the closed end to the open end;
    an applicator head sitting on the open end of the pen body, the applicator head having, a porous material, wherein the applicator head has an end section that fits into the open end of the pen body; and
    mechanical fastening means for positive-locking and/or friction-locking engagement with the outer circumference of the end section of the applicator head are provided on the pen body, and configured to bring about the positive-locking and/or friction-locking engagement without deformation of the end section of the applicator head protruding into the open end of the pen body,
    wherein an outer surface of a wall of the pen body is structured with at least one recess configured with an edge for rupturing the ampule when received within the pen body, the edge extending in a direction transverse to the longitudinal direction of the application pen, and
    wherein the at least one recess extends circumferentially about the outer surface of the wall of the pen body.

2. The application pen according to claim 1, wherein the applicator head has a prismatic or cylindrical basic shape in the inserted state.

3. The application pen according to claim 1, wherein the wall of the pen body is sufficiently flexible to break the ampule when received within the pen body, and as a result bring about discharge of liquid from the ampule into an interior of the pen body.

4. The application pen according to claim 3, wherein the outer surface of the wall of the pen body is structured with at least one elevation.

5. The application pen according to claim 4, wherein the outer surface of the wall of the pen body has a plurality of annular recesses which mark a constriction region of the pen body.

6. The application pen according to claim 4, wherein symbols are formed into the outer surface of the wall of the pen body, the symbols being configured to guide a user to exert local pressure on the pen body in order to break the ampule.

7. The application pen according to claim 3 wherein, close to the open end of the pen body, a plurality of annular recesses is provided and define a gripping area of the application pen.

8. A method for manufacturing an application pen comprising:
    preparing a pen body made of plastic, the pen body having a closed and an open end, a longitudinal direction of the application pen extending from the closed end to the open end,
    preparing an applicator head which includes a foam, felt or fiber body, with an end section that fits into the open end of the pen body, filling the pen body with an ampule containing a liquid, and inserting and mechanically fastening the applicator head in the open end of the pen body, wherein an outer surface of a wall of the pen body is structured with at least one recess configured with an edge for rupturing the ampule when received within the pen body, the edge extending in a direction transverse to the longitudinal direction of the application pen, and wherein the at least one recess extends circumferentially about the outer surface of the wall of the pen body.

9. The method according to claim 8, wherein the mechanical fastening consists of an insertion or rotation of the applicator head into the pen body from the open end, without deformation of a basic shape of the applicator head.

10. The method according to claim 8, wherein the mechanical fastening comprises:
a first partial step of resistance-free insertion into the open end of the pen body in an inoperative initial state of mechanical fastening means provided there, and
a second partial step of transferring the mechanical fastening means into a state of engagement with the end section of the applicator head in order to establish a positive and/or friction lock.

11. The application pen according to claim 1, wherein the porous material is a foam, felt or fiber body.

12. The application pen according to claim 1, wherein the at least one recess is annular.

13. The application pen according to claim 1 wherein the application pen is configured for dispensing liquid, when received, in a planar manner.

14. An application pen manufactured according to a method comprising the following steps:
preparing a pen body made of plastic, the pen body having a closed and an open end, a longitudinal direction of the application pen extending from the closed end to the open end,
preparing an applicator head which includes a foam, felt or fiber body, with an end section that fits into the open end of the pen body,
filling the pen body with an ampule containing a liquid, and
inserting and mechanically fastening the applicator head in the open end of the pen body, wherein an outer surface of a wall of the pen body is structured with at least one recess configured with an edge for rupturing the ampule when received within the pen body, the edge extending in a direction transverse to the longitudinal direction of the application pen, and
wherein the at least one recess extends circumferentially about the outer surface of the wall of the pen body.

15. The application pen according to claim 1, wherein at least the end section of the applicator head and at least the open end of the pen body are cylindrical in shape, and the fastening means is an inner thread on the pen body, the fastening means cutting into a circumference of the end section of the applicator head.

16. The method according to claim 8, wherein the inserting and mechanically fastening include inserting and mechanically fastening the applicator head in the open end of the pen body by a fastening means, wherein at least the end section of the applicator head and at least the open end of the pen body are cylindrical in shape, and the fastening means have an inner thread on the pen body, the fastening means cutting into a circumference of the end section of the applicator head.

17. The application pen according to claim 14, wherein the inserting and mechanically fastening include inserting and mechanically fastening the applicator head in the open end of the pen body by a fastening means, wherein at least the end section of the applicator head and at least the open end of the pen body are cylindrical in shape, and the fastening means have an inner thread on the pen body, the fastening means cutting into a circumference of the end section of the applicator head.

18. An application pen according to claim 1, comprising in combination:
an ampule containing liquid, the ampule being configured for receipt and rupture within the hollow pen body.

19. The application pen according to claim 1, wherein the at least one recess configured with the edge for rupturing the ampule when received within the pen body includes only a single recess.

* * * * *